(12) United States Patent
Lombard et al.

(10) Patent No.: US 10,888,452 B2
(45) Date of Patent: Jan. 12, 2021

(54) WEARABLE THERMAL GEL-PACK

(71) Applicant: Elite Fighting Championship LLC, Boca Raton, FL (US)

(72) Inventors: Hector Lombard, Boca Raton, FL (US); Francisco Molina, Fort Lauderdale, FL (US)

(73) Assignee: The Gym Lombard LLC, Boynton Beach, FL (US)

( * ) Notice: Subject to any disclaimer, the term of this patent is extended or adjusted under 35 U.S.C. 154(b) by 73 days.

(21) Appl. No.: 15/431,126

(22) Filed: Feb. 13, 2017

(65) Prior Publication Data

US 2018/0228645 A1 Aug. 16, 2018

(51) Int. Cl.
*A61F 7/02* (2006.01)
*A61F 7/10* (2006.01)
*A61F 7/00* (2006.01)

(52) U.S. Cl.
CPC ............... *A61F 7/02* (2013.01); *A61F 7/10* (2013.01); *A61F 7/103* (2013.01); *A61F 2007/0087* (2013.01); *A61F 2007/0219* (2013.01); *A61F 2007/0228* (2013.01)

(58) Field of Classification Search
CPC ............... A61F 2007/0087; A61F 7/02; A61F 2007/0219; A61F 2007/022; A61F 2007/0225; A61F 2007/0226; A61F 2007/0228; A61F 2007/023; A61F 2007/0231; A61F 2007/0257; A61F 2007/0269; A61F 2007/0277; A61F 7/10; A61F 2007/0244; A61F 7/103; A61F 2007/105; A61F 2007/108
See application file for complete search history.

(56) References Cited

U.S. PATENT DOCUMENTS

| | | | | |
|---|---|---|---|---|
| 4,758,217 A | * | 7/1988 | Gueret | A61F 7/10 604/291 |
| 5,514,170 A | * | 5/1996 | Mauch | A61F 7/10 126/204 |
| 5,840,080 A | * | 11/1998 | Der Ovanesian | A61F 7/02 607/114 |
| 6,093,202 A | * | 7/2000 | Dyken | A61F 7/02 607/108 |

(Continued)

*Primary Examiner* — Kaitlyn E Smith
*Assistant Examiner* — Bradford C. Blaise
(74) *Attorney, Agent, or Firm* — Mark C. Johnson; Johnson Dalal

(57) ABSTRACT

A wearable thermal gel-pack comprising a gel-pack body having a first portion including an inner surface and defining a gel cavity encapsulating a gel material therein and a second portion including a container with a first member coupled to the first portion, a second member pivotally coupled to the first member to form a joint and with an outer surface opposing the inner surface of the first portion, and a container cavity defined by the first and second members, the container cavity juxtaposed to and fluidly uncoupled to the gel cavity, the first and second members of the container having a closed position with a watertight configuration and an open position with a container opening in fluid communication with the container cavity and a strap couplable to the second member at a location along a strap length and operably configured to surround the inner surface of the first portion.

17 Claims, 12 Drawing Sheets

(56) References Cited

U.S. PATENT DOCUMENTS

| | | | | |
|---|---|---|---|---|
| 2002/0052569 A1* | 5/2002 | Horning | ................... | A61F 7/10 602/41 |
| 2010/0217363 A1* | 8/2010 | Whitely | ................... | A61F 7/02 607/112 |
| 2015/0080827 A1* | 3/2015 | Fogg | ...................... | A61F 13/84 604/377 |
| 2016/0287431 A1* | 10/2016 | Hixson, Jr. | ............... | A61F 7/10 |

* cited by examiner

WEARABLE THERMAL GEL-PACK

FIELD OF THE INVENTION

The present invention relates generally to gel-packs, and, more particularly, relates to a wearable thermal gel-pack for supplying pain-relieving hot or cold therapy.

BACKGROUND OF THE INVENTION

It is well known that participating in sports, weightlifting, and other recreational activities leads to occasional injuries. These injuries frequently result in inflammation and swelling. Applying ice, gel, or another cold substance to an injured area produces therapeutic benefits, including, but not limited to, reduced pain, inflammation, and swelling. Such therapeutic benefits are produced by slowing down blood flow to the injured area, i.e., slowing blood circulation. The application of the cold substance to the injured area is often referred to as "cold therapy" or "cryotherapy." Cold therapy is beneficial for treating sprains, strains, bumps, bruises, and the like.

At least one known method of applying cold therapy to an injured area is through the use of a plastic bag filled with ice. The ice-filled plastic bag is not only uncomfortable to hold with a bare hand due to the temperature, but is also challenging to hold against the injured area because the shape of the ice does not allow the ice to lay flat against the injured area. Moreover, when the ice-filled plastic bag is wrapped with a thin paper towel, the paper towel often disintegrates, thus not only creating a messy area, but also requiring frequent replacement. As an added problem, paper towels that are relatively thick produce a thermal insulation effect, thereby reducing the benefits of the cold therapy. As a further disadvantage, the plastic bag cannot be conveniently strapped to or otherwise worn by the user when performing desired activities.

Another known method of applying cold therapy to the injured area is through the use of an ice pack. The application of an ice pack to the injured area may cause ice burns, especially when there is no barrier between the ice pack and a user's skin. Similar to ice-filled plastic bags, ice packs are often uncomfortable to manually hold and do not allow a user to strap the ice pack directly to the user's body part so that the user can move about when applying the ice pack to the injury.

Heat therapy, often referred to as "thermotherapy," is frequently used for rehabilitation purposes. Applying heat to an injured area beneficially produces therapeutic benefits, including, but not limited to, increasing the extensibility of collagen tissues, decreasing joint stiffness, reducing pain, relieving muscle spasms, increasing blood flow, and the like.

At least one known method of applying heat therapy to the injured area is through the use of a hot cloth. The hot cloth is often uncomfortable for the user to manually hold, especially for extended periods of time, e.g., 20-30 minutes. Another known method of applying heat therapy is through the use of various types of heating pads. Unfortunately, electric heating pads only maintain a constant level of heat so long as they are connected to a power source. Obviously, remaining connected to a power source is inconvenient as the user cannot apply the heat therapy while at remote locations. Moreover, electric heating pads and portable heating pads, which utilize a portable power source such as a battery, present a risk of electric shock, skin burns, and fire accidents.

Therefore, a need exists to overcome the problems with the prior art as discussed above.

SUMMARY OF THE INVENTION

The invention provides a thermal gel-pack that overcomes the hereinafore-mentioned disadvantages of the heretofore-known devices and methods of this general type and which not only includes a thermal gel-pack body configured to supply hot and/or cold pain-relief therapy using a gel cavity and a container cavity suitable for storing ice therein, but may also be conveniently worn by a user using a strap couplable to the thermal gel-pack body.

With the foregoing and other objects in view, there is provided, in accordance with the invention, a wearable thermal gel-pack having a gel-pack body with a first portion including an inner surface and defining a gel cavity, wherein the first portion encapsulating a gel material within the gel cavity. The gel-pack body also has a second portion including a container with a first member coupled to the first portion of the gel-pack body, a second member pivotally coupled at a proximal end of the first member to form a joint and with an outer surface opposing the inner surface of the first portion of the gel-pack body, and a container cavity defined by the first and second members of the container. The container cavity is juxtaposed to and fluidly uncoupled to the gel cavity, wherein the first and second members of the container have a closed position with a watertight configuration with respect to one another and are operably configured to pivotally translate about the joint to have an open position with a container opening at least partially defined by a distal end of the first member and a distal end of the second member and in fluid communication with the container cavity. The device may also have a strap couplable to the outer surface of the second member at a location along a strap length and operably configured to surround the inner surface of the first portion.

In accordance with a further feature of the present invention, the first portion includes a front surface opposing the inner surface of the first portion such that the inner surface is interposed between the front surface of the first portion and the outer surface of the second member of the second portion, the front surface of an elastically deformable material.

In accordance with yet another feature of the present invention, the gel cavity is interposed between the front surface and the inner surface of the first portion.

In accordance with an additional feature of the present invention, the container cavity is interposed between the inner surface of the first portion and the outer surface of the second member of the second portion.

In accordance with a further feature of the present invention, the gel material is one of hydroxyethyl cellulose, silica gel, and polymer.

In accordance with another feature of the present invention, the strap is removably couplable to the outer surface of the second member.

In accordance with another feature, an embodiment of the present invention includes a loop coupled to the outer surface of the second member, wherein the loop sized to receive the strap therein along the strap length such that strap is operably configured to surround the inner surface of the first portion and a user's limb.

In accordance with yet another feature, an embodiment of the present invention also includes a handle coupled to the outer surface of the second member, wherein the handle defines a handle aperture configured to receive a portion of a user's hand therein. Additionally, the handle may include an adjustable handle strap defining an adjustable circumference of the handle aperture.

In accordance with the present invention, a wearable thermal gel-pack is also disclosed that includes a gel-pack body with a first portion having a user contact surface and an inner surface opposite the user contact surface, wherein the user contact surface and the inner surface define a gel cavity for encapsulating a gel material within the gel cavity. The gel-pack body also includes a second portion having a container, wherein the container includes a first member coupled to the first portion of the gel-pack body and a second member pivotally coupled at a proximal end of the first member to form a joint, wherein the second member having an outer surface opposing the inner surface of the first portion of the gel-pack body. The device also includes a container cavity defined by the first and second members of the container, wherein the container cavity is substantially adjacent to and fluidly uncoupled to the gel cavity. The first and second members of the container have a closed position with a watertight configuration with respect to one another and are operably configured to pivotally translate about the joint to have an open position with a container opening at least partially defined by a distal end of the first member and a distal end of the second member, wherein the container opening is in fluid communication with the container cavity. The device may also have a loop coupled to the outer surface of the second member, wherein the loop is sized to receive a strap therein along a strap length. The strap is operably configured to couple the user contact surface of the first portion to a portion of a user's limb.

In accordance with another feature, the present invention includes the user contact surface of the first portion being of an elastically deformable material.

Although the invention is illustrated and described herein as embodied in a wearable thermal gel-pack, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
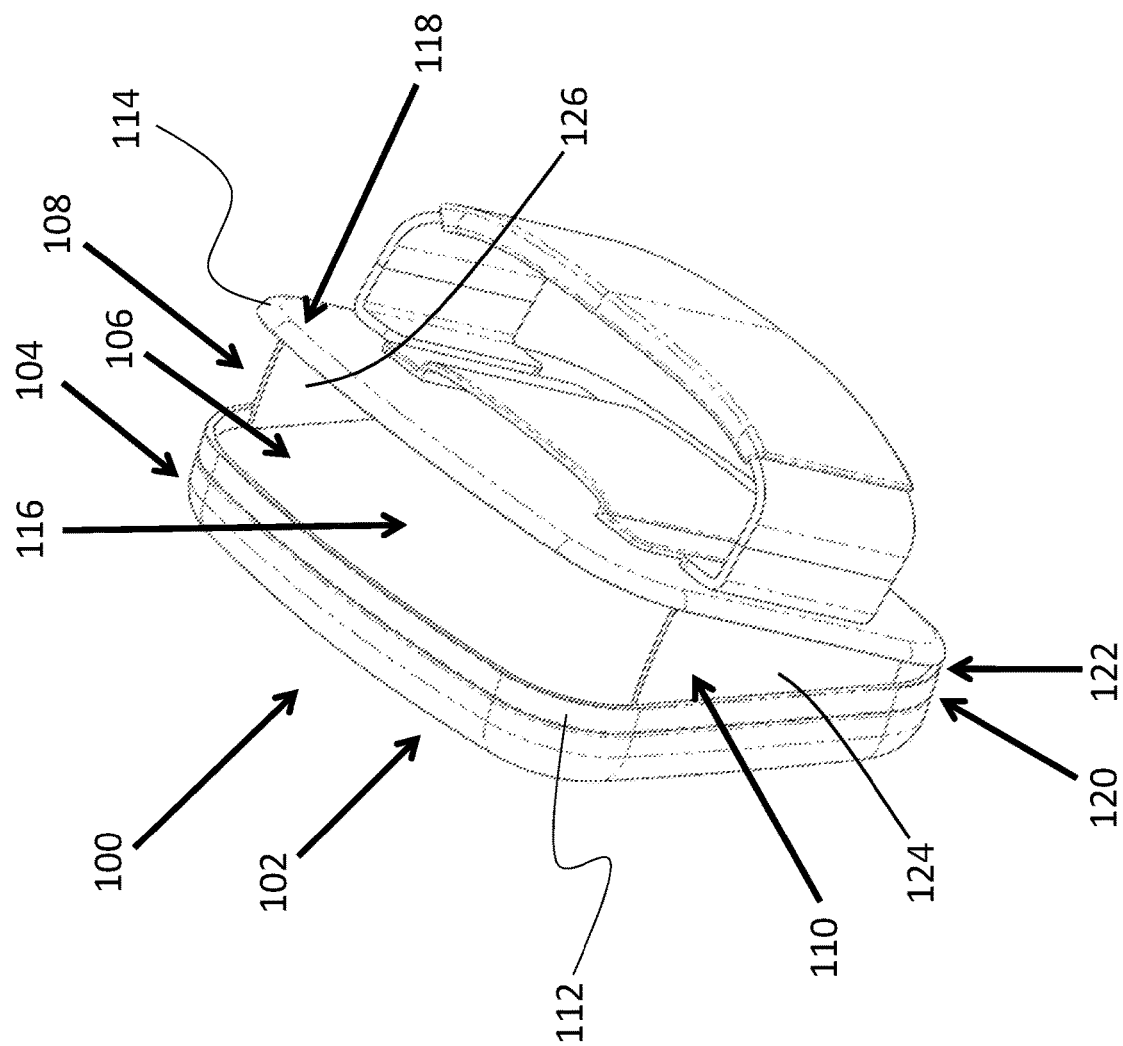
FIG. 1 is a perspective rear view of a wearable thermal gel-pack including a gel-pack body having a first portion and a second portion, the second portion including a container having a first member and a second member defining a container cavity in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient wearable thermal gel-pack having a first portion including a gel cavity encapsulating a gel material therein and a second portion fluidly uncoupled from the first portion and including a container for storing a cold constituent, such as ice, therein. Advantageously, the gel material may be heated or in a preferred embodiment, may be frozen, to effectively supply hot or cold pain-relief therapy to a user's injured limb. Embodiments of the invention provide the container having a closed position with a watertight configuration and an open position for depositing ice within the container. In addition, embodiments of the invention include the gel-pack having a strap for surrounding a user's injured limb, thereby providing the user with the ability to perform various tasks without the need to manually hold the thermal gel-pack strap.

Figure 2:
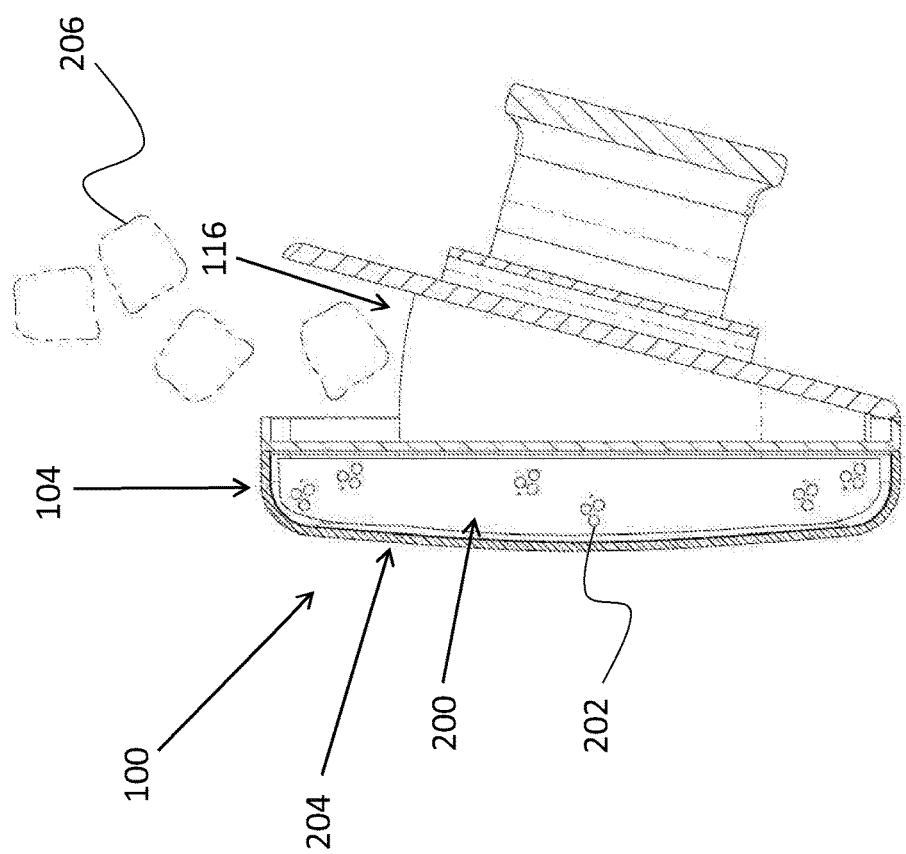
FIG. 2 is an elevational side view of the gel-pack of FIG. 1 depicting a gel cavity encapsulating a gel material therein and a plurality of ice cubes for disposal within the container cavity in accordance with the present invention.

Referring now to FIG. 1, one embodiment of the present invention is shown in a perspective rear view. FIG. 1 shows several advantageous features of the present invention, but, as will be described below, the invention can be provided in several shapes, sizes, combinations of features and components, and varying numbers and functions of the components. The first example of a wearable thermal gel-pack 100, as shown in FIG. 1, includes a gel-pack body 102 having a first portion 104 including an inner surface 106. With brief reference to FIG. 2, depicting an elevational side view of the thermal gel-pack 100, the first portion 104 can be seen defining a gel cavity 200 and encapsulates a gel material 202 disposed within the gel cavity 200. The term "encapsulate" is defined herein as having a referencing article, e.g., one or more surfaces of the front portion 104, completely surrounding the gel cavity 200 on all sides. The encapsulated gel material 202 may be, without limitation, hydroxyethyl cellulose, silica gel, a polymer, or another material suitable for sustaining a hot or cold temperature. In one embodiment, the gel material 202 may occupy an entire volume of the gel cavity 200. In another embodiment, the gel material 202 may occupy a portion, e.g., less than 75% of the volume of the gel cavity 200. In other embodiments, the gel material 202 may occupy greater than 75% of the volume of the gel cavity 200 but less than the entire volume of the gel cavity 200.

In a preferred embodiment, the gel cavity 200 is interposed between a front surface 204 of the first portion 104 and the inner surface 106 (FIG. 1) of the first portion 104, however in other embodiments, other components of the thermal gel-pack 100 may surround and/or define the gel cavity 200. Accordingly, the gel material 202 may be in contact with the front surface 204 which is operably configured to be disposed adjacent a user's injured limb. As such, the front surface 204 may be referred to as a user-contact surface. The term "injured limb" is defined herein in its broadest possible sense and may include, without limitation, the user's arm, leg, ankle, back, or another area of the user's body that would benefit from the application of heat or ice applied thereto. In use, the user may secure the front surface 204 adjacent to the injured limb using a handle and/or a strap 800 (FIG. 8), as will be explained in further detail herein. The gel material 202 may be heated or the thermal gel-pack strap 100 may be filled with ice to advantageously supply hot or cold pain-relief therapy to the injured limb.

Figure 3:
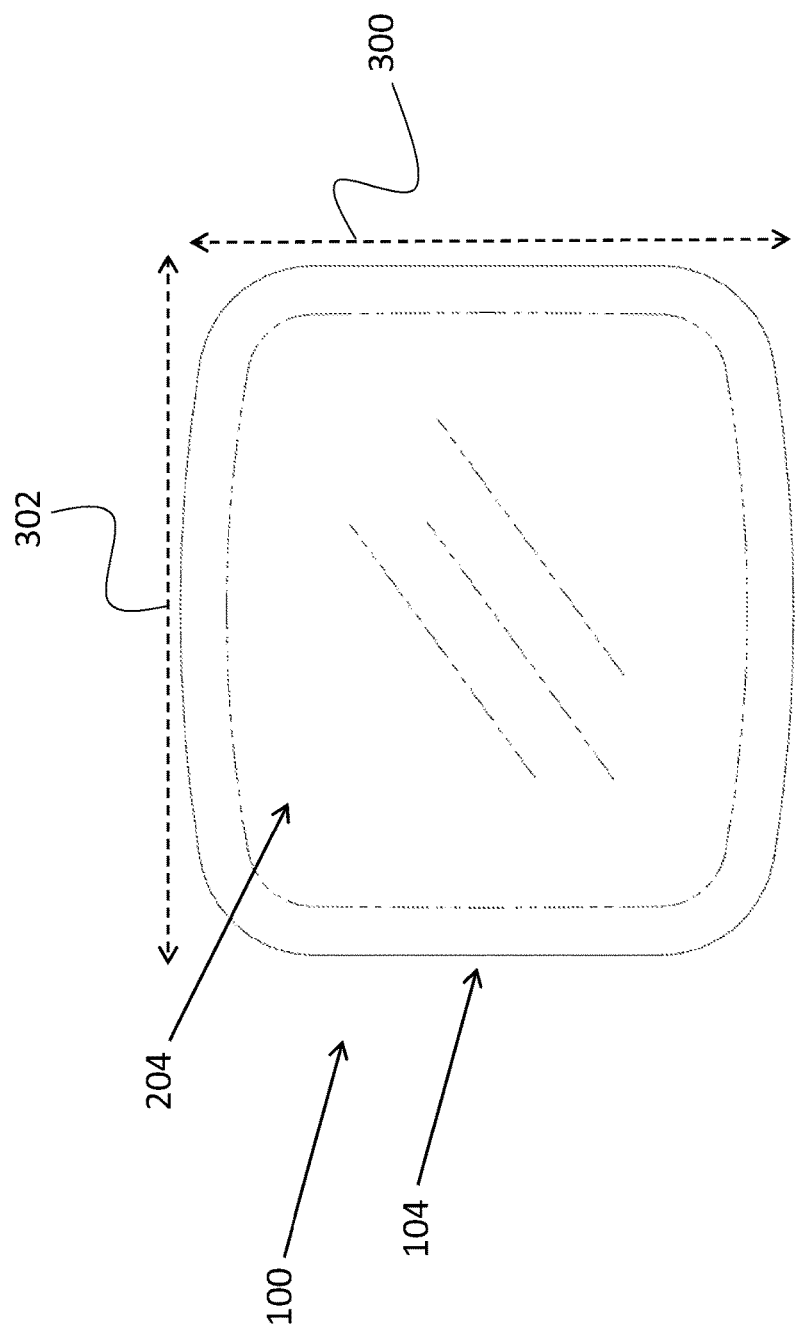
FIG. 3 is an elevational front view of a front surface of the first portion of the gel-pack body of FIG. 1 in accordance with an exemplary embodiment of the present invention.

With brief reference to FIGS. 1 and 3, in one embodiment, the front portion 104, more specifically, the inner surface 106 (FIG. 1) and the front surface 204 (as best shown in FIG. 3), may be made of an elastically deformable material that exhibits the ability to change its shape and return back to its static-state shape after its change in shape. Advantageously, the elastically deformable material provides the user with a front surface 204 that is flexible and deformable, therefore reducing the risk of subjecting the injured limb to increased pressure and pain that typically occurs when using a stiff and unyielding front surface 204. As an added advantage, the front surface 204 provides a protective barrier between the user's skin and the gel material 202 to decrease the risk of skin burns while simultaneously and effectively producing hot or cold therapy. In one embodiment, the front portion 104 may be made of PVC plastic. In other embodiments, the front portion 104 may be made of neoprene, a composite material, a fabric material, or another material that may or may not have deformable elastic properties.

As best shown in FIG. 3, in one embodiment, the front portion 104 includes a front portion height 300 of approximately 4-6 inches and a front portion length 302 of approximately 4-6 inches. In other embodiments, the front portion height 300 and the front portion length 302 may be outside of these ranges. The front portion height 300 and the front portion length 302 may be approximately the same dimensions or may differ from each other. For example, in one embodiment, the front portion height 300 may be approximately 4 inches and the front portion length 302 may be approximately 4.5 inches.

With reference again to FIG. 1, the gel-pack body 102 is depicted having a second portion 108 including a container 110. Naturally, the second portion 108 may be the first portion 104 and the first portion 104 may be the second portion 108. In the same vein, the gel-pack body 102 may be unitary, i.e., the first and second portions 104, 108 may be fixedly coupled with respect to each other, or may be non-unitary, i.e., provided as separate components.

In one embodiment, the container 110 of the second portion 108 includes a first member 112 and a second member 114 which define a container cavity 116. Generally speaking, the container cavity 116 is the opening interposed between the inner surface 106 of the first portion 104 and an outer surface 118 of the second member 114 of the second portion 108. In other embodiments, the container cavity 116 may be defined by other components of the thermal gel-pack 100.

In one embodiment, the first member 112 is coupled to the first portion 104 of the gel-pack body 102 and the second member 114 is pivotally coupled at a proximal end 120 of the first member 112 to form a joint 122. The term "joint" is defined herein as the location in which the first and second members 112, 114 are joined in such a way so as to permit motion between the first and second members 112, 114. The joint 122 advantageously allows the second member 114 to move in a direction toward and away from the inner surface 106 of the first portion 104 to seal and expose the container cavity 116. The joint may be, without limitation, a hinge joint, pivot join, or the like. In other embodiments, the second member 114 may be removably decoupled from the first member 112. In any event, the first and second members 112, 114 may twist, snap, rotate, or otherwise couple and uncouple from each other to expose and seal the container cavity 116. As seen in FIG. 1, each of the opposing sides of the first and second members 112, 114 are coupled with a side coupling material 124, 126 having opposing ends coupled to the first and second members 112, 114 of the second portion 108, respectively. As seen in FIG. 1, the container opening 400 (as best seen in FIG. 4) is defined by a continuous perimeter spanning from each distal end, and around opposing sides, of the members 112, 114 of the second portion 108 until reaching the joint 122.

With reference now to FIG. 2, the container cavity 116 is advantageously configured to be filled with one or more pieces of ice 206 or another solid or liquid substance, e.g., water which may thereafter be frozen, to supply cold therapy. In a preferred embodiment, the container cavity 116 is juxtaposed to, i.e., substantially adjacent, and fluidly uncoupled to the gel cavity 200. The term "fluidly uncoupled" is defined herein as preventing fluid exchange between the container cavity 116 and the gel cavity 200. When desired for use, one exemplary method includes a user filling or inserting one or more pieces of ice within the container cavity 116. The dividing surface, e.g., inner surface 106, between the container cavity 116 and the gel cavity prevents the fluid generated from the ice to transfer to the gel cavity 200. The inner surface 106, like the outer surface 204, may be elastically deformable so as to allow the ice 206 to protrude in the first portion 104. The inner surface 106 may also be of a material that facilitates in permitting a more efficient thermal heat transfer, e.g., from the gel material 202 to the ice 206, than convention plastic or polymer-based plastics (e.g., having a temperature gradient between the material of the inner surface 106 within 10-15° F.). In preferred embodiments, the material is generally considered to be a thermal conductor again compared to convention plastic materials. One such material is an elastomer sold by the company Celanese under the trademark or trade name, COOLPOLY. In this way, the gel material 202 may be maintained at a lower temperature for a longer period of time, thus providing users greater therapeutic benefits when exposing the wearable gel-pack to the injured area.

Figure 4:
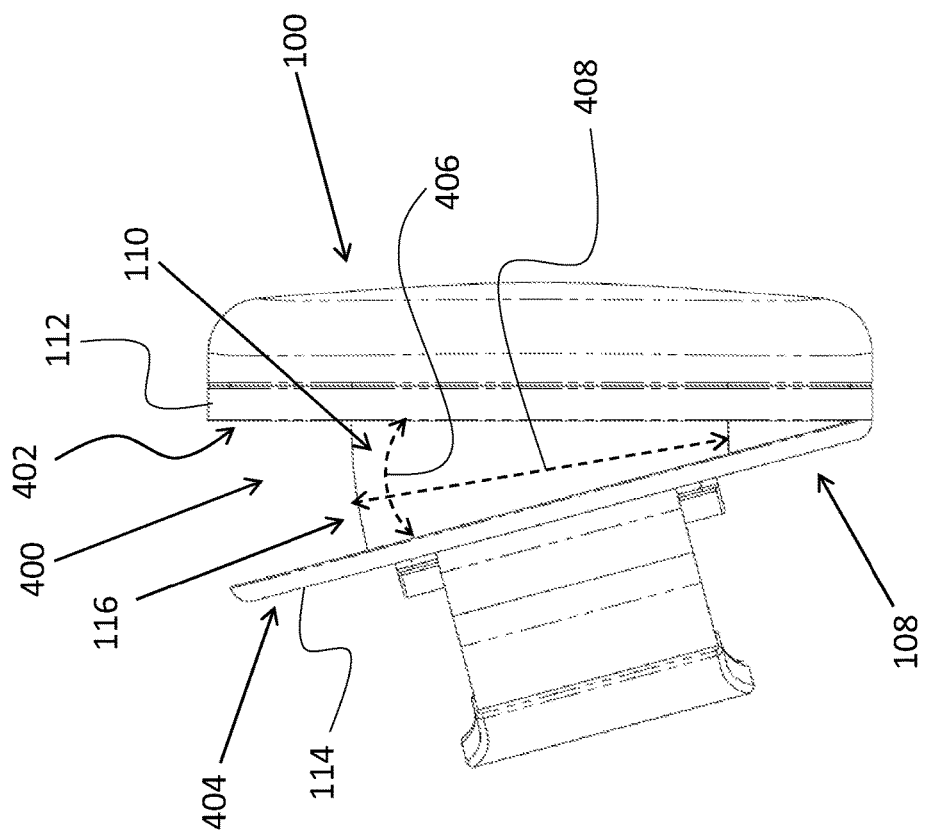
FIG. 4 is an elevational side view of the gel-pack of FIG. 1 depicting a container opening in fluid communication with the container cavity.

With reference now to FIG. 4, the thermal gel-pack 100 is depicted in an elevational side view. Similar to FIGS. 1 and 2, FIG. 4 depicts the first and second members 112, 114 of the container 110 having an open position. In one embodiment, the open position includes a container opening 400 at least partially defined by a distal end 402 of the first member 112 and a distal end 404 of the second member 114. In order to provide a user with the ability to easily and conveniently deposit the ice cubes 206 into the container cavity 116, the container opening 400 may be in fluid communication with the container cavity 116. In one embodiment, the container 110 includes a container width 406 of approximately 1-2 inches. In other embodiments, the container width 406 may be outside of this range. In the same vein, the container 110 may include a container height 408 that is approximately 2-4 inches, depending on the overall height of the second portion 108. Referring to FIG. 1 and FIG. 4, the first and second members 112, 114 can also be seen having side coupling material with opposing ends coupled thereto and located proximal to opposing sides of the first and second members, thereby being configured (as seen best in FIG. 2) to resist ice 206 inserted into the container opening 400 from exiting from the opposing sides of the first and second members 112, 114 when opened. Also when opened, the container opening 400 can be seen being continuously defined by and spanning the continuous outer perimeter edges on the first and second members 112, 114 of the second portion and with the continuous outer perimeter edges on the first and second members 112, 114 of the second portion separated from one another around the opposing sides and the distal ends 402, 404 of the first and second members 112, 114 of the second portion 108 until reaching the joint where the first and second members 112, 114 pivot with respect to one another.

Figure 5:
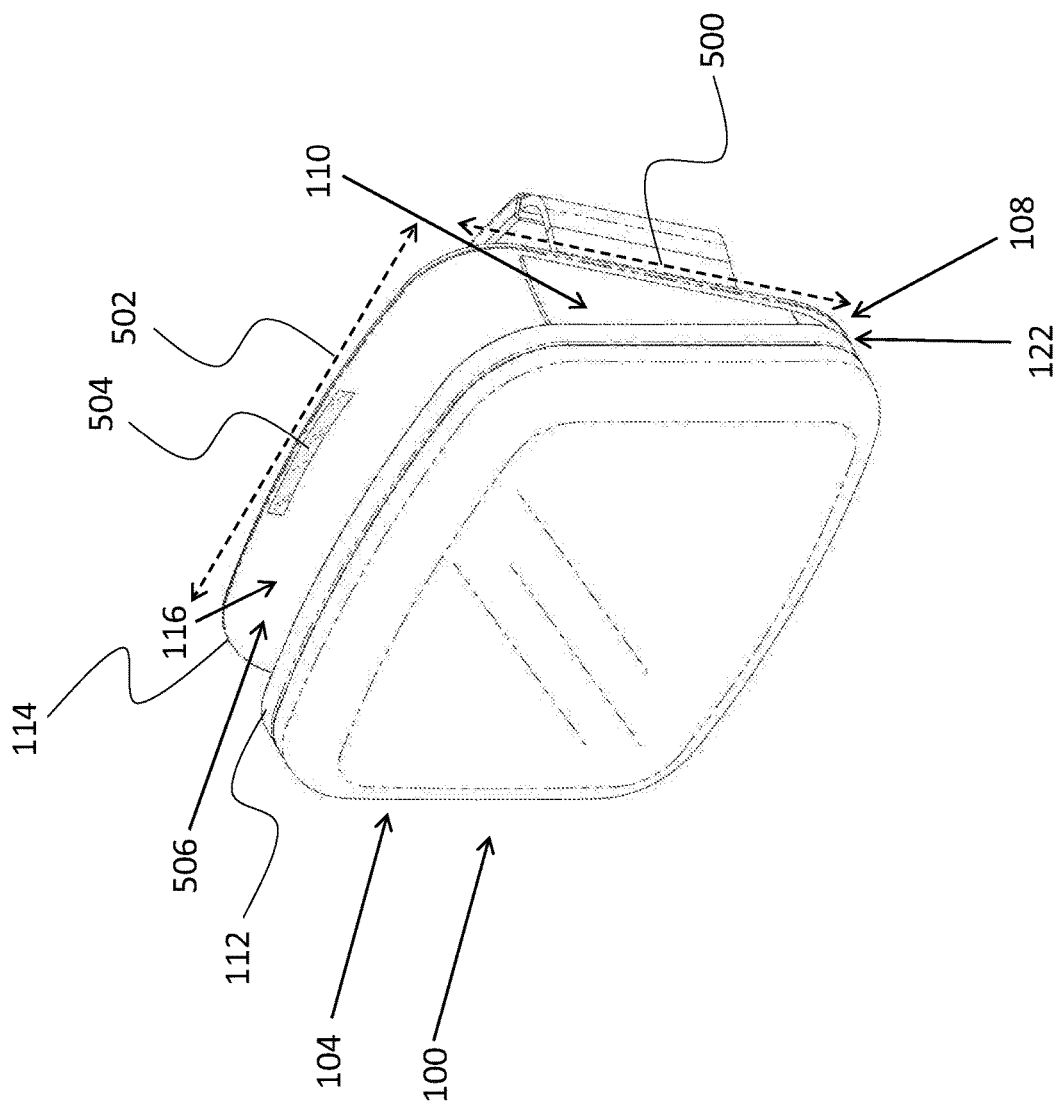
FIG. 5 is a perspective front view of the gel-pack of FIG. 1 depicting the container in an open position and including the second portion having a fastener operably configured to secure the container in a closed position.

With reference to FIG. 5, the second portion 108 is depicted including a second portion height 500 of approximately 4-6 inches and a second portion length 502 of approximately 4-6 inches. In other embodiments, the second portion height 500 and the second portion length 502 may be outside of these ranges. In a preferred embodiment, the second portion height 500 and the second portion length 502 are the approximately the same as the front portion height 300 and the front portion length 302, however, the dimensions of the respective first and second portions 104, 108 may differ from each other.

Figure 6:
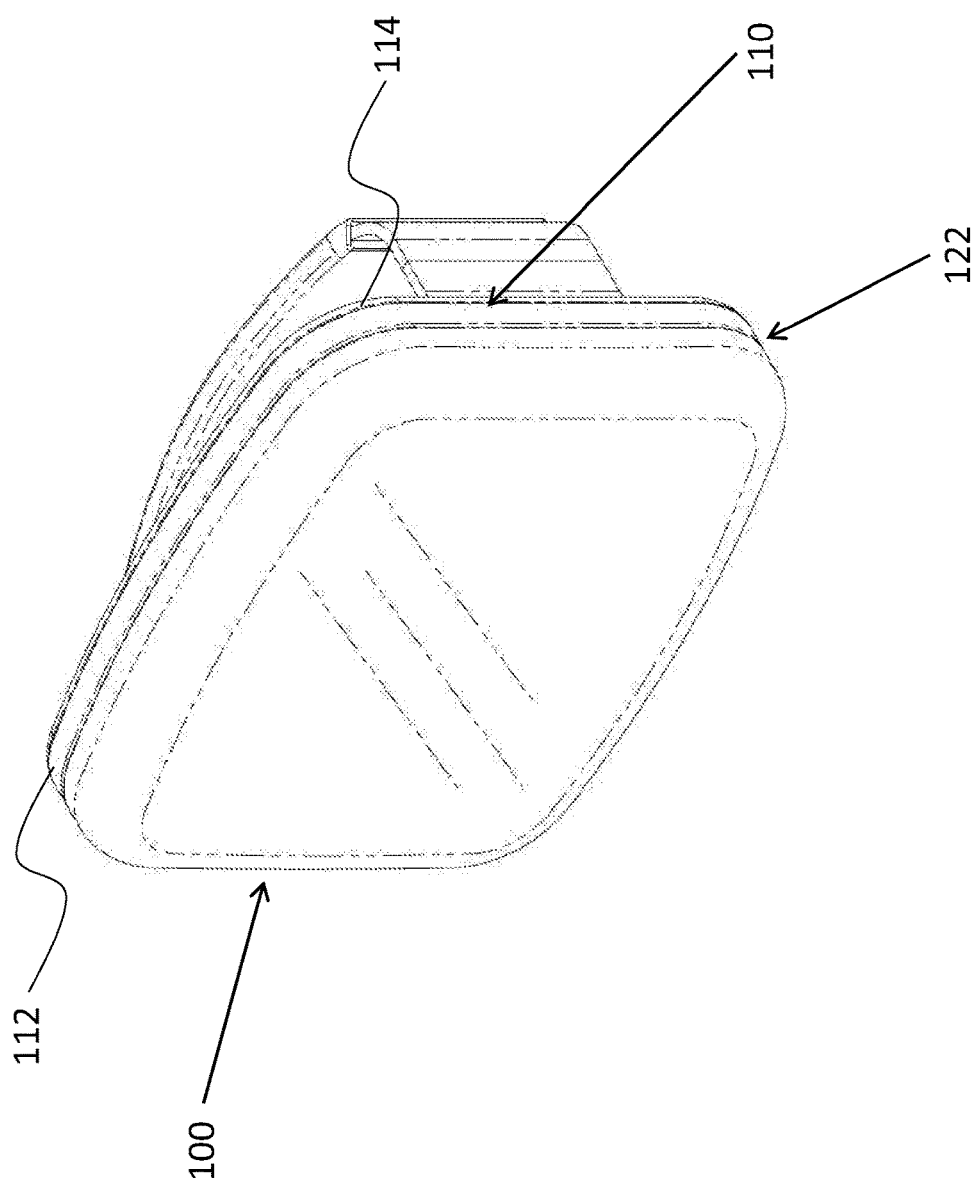
FIG. 6 is perspective front view of the gel-pack of FIG. 1 depicting the container in a closed position in accordance with an exemplary embodiment of the present invention.
Figure 7:
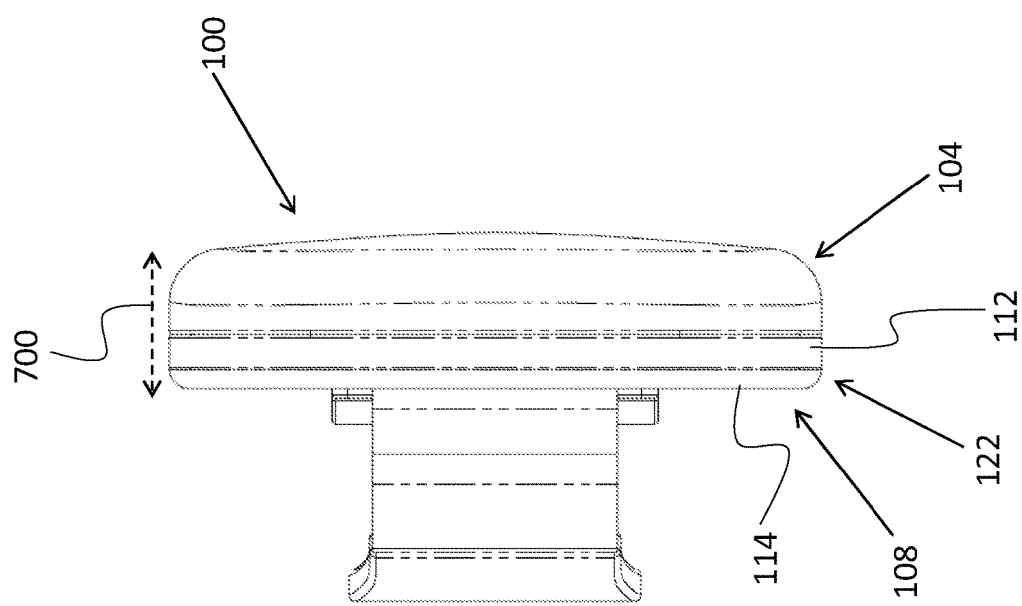
FIG. 7 is an elevational side view of the gel-pack of FIG. 1 depicting the container in the closed position in accordance with an exemplary embodiment of the present invention.

With reference now to FIGS. 5 through 7, the thermal gel-pack 100 is depicted including the first and second members 112, 114 having the open position (FIG. 5) and a closed position (FIGS. 6 and 7), respectively. In order to translate the first and second members 112, 114 from the open position to the closed position, in one embodiment, the first and second members 112, 114 are operably configured to pivotally translate about the joint 122. This joint 122 may extend along the entire length 502 of the members 112, 114 or may be located along a portion of the length 502. The cavity 116, however, should still be watertight when the members 112, 114 are in the closed position. Advantageously, as shown in FIG. 5, in order to maintain the closed position of the container 110, in one embodiment, the second member 114 of the container 110 includes a fastener 504 coupled to a second member inner surface 506. The fastener 504 may be, without limitation, a hook and loop material, adhesive, or the like. The inner surface 506 may be made of an isolated foil, plastic, or another material suitable for enhancing the thermal insulation properties of the container 110. In the closed position, in a preferred embodiment, the first and second members 112, 114 include a watertight configuration with respect to one another. As such, the user is advantageously provided with a thermal gel-pack 100 that not only includes thermal retention properties but also seals water, or another liquid, within the container 110. As best shown in FIG. 7, in the closed position, in one embodiment, the first and second portions 104, 108 may include a width 700 of approximately 0.5 of an inch to 1.0 inch. In other embodiments, in the closed position, the width 700 may be outside of this range.

Figure 8:
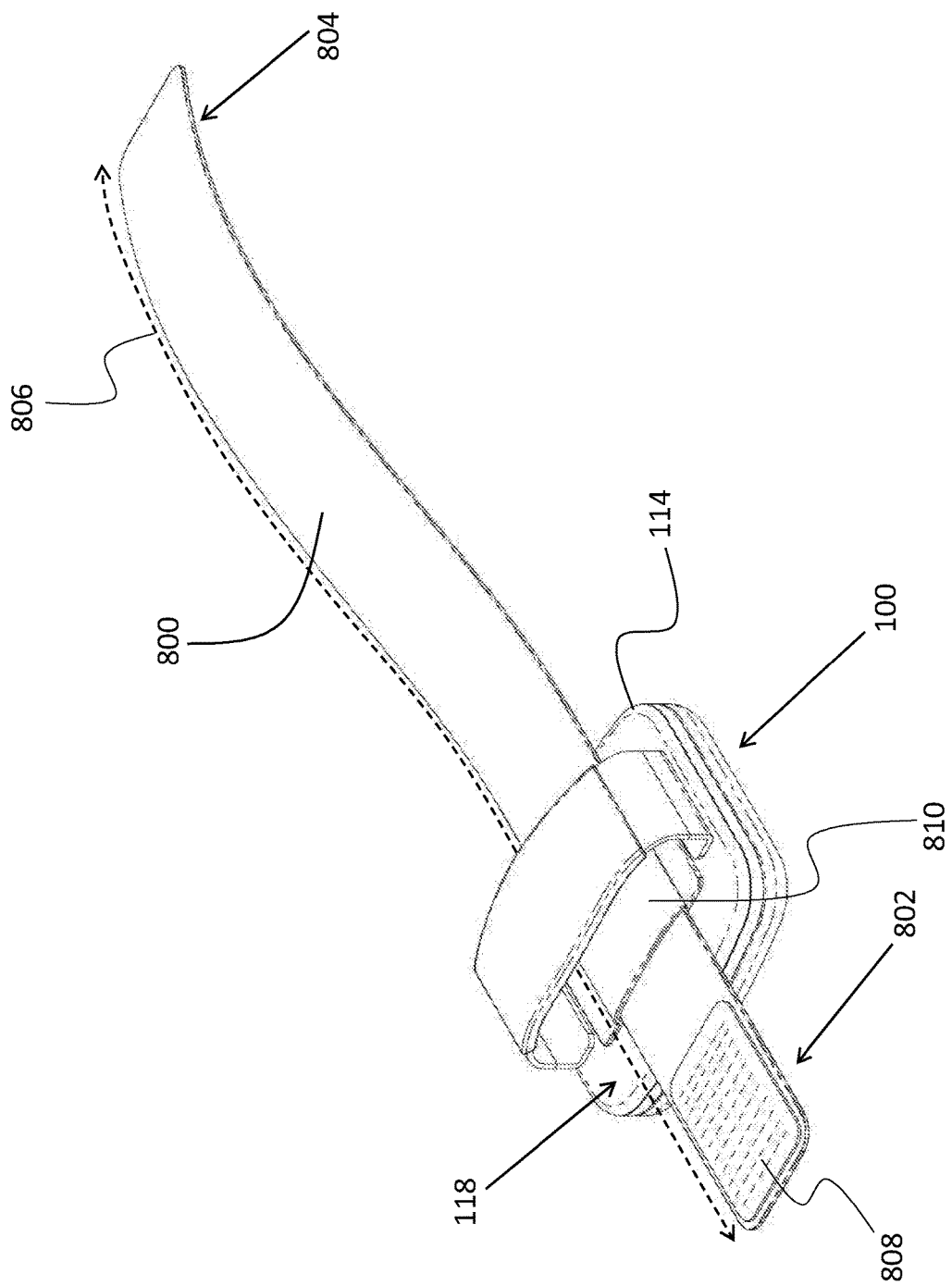
FIG. 8 is a perspective rear view of the gel-pack of FIG. 1 depicting a strap coupled to the gel-pack body and having a fastener coupled thereto in accordance with the present invention.
Figure 9:
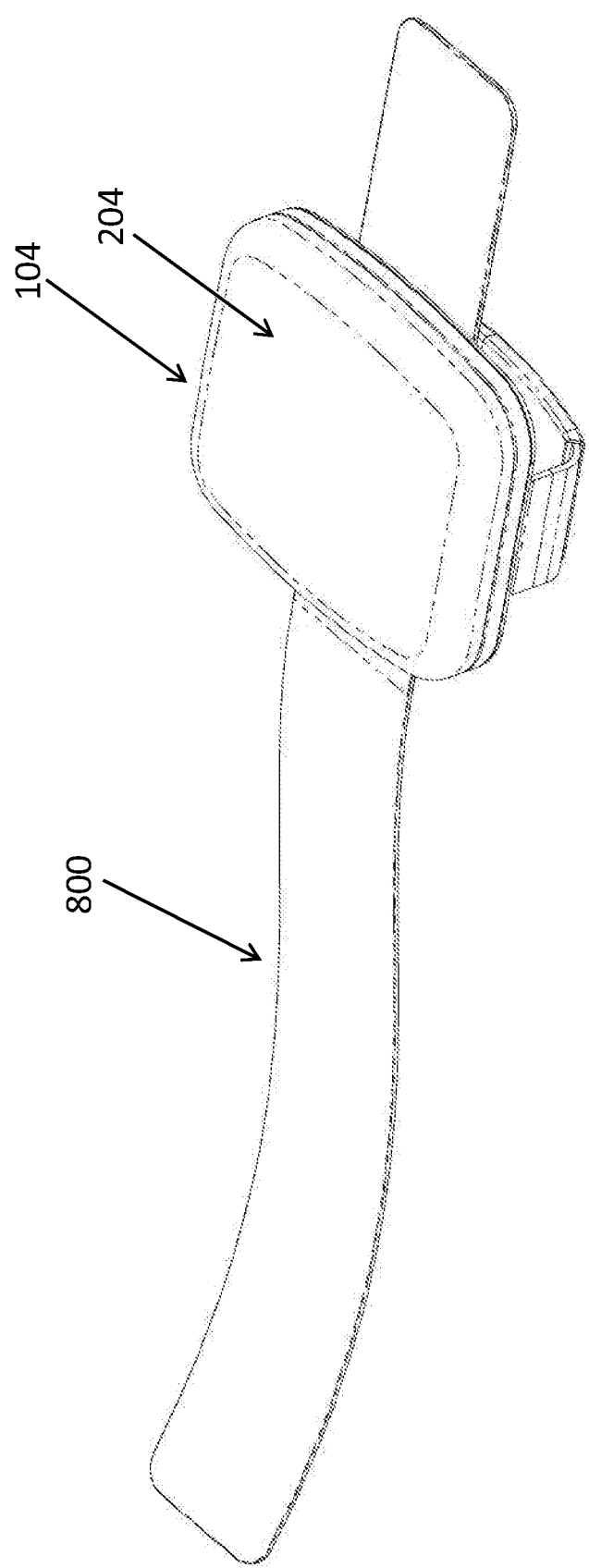
FIG. 9 is a perspective front view of the gel-pack of FIG. 1 depicting the strap coupled to the gel-pack body in accordance with the present invention.

With reference now to FIG. 8, the thermal gel-pack 100 is depicted including a strap 800 having a first end 802 and a second end 804 opposite from the first end 802 along a strap length 806. In one embodiment, the length 806 of the strap 800 is approximately 10-15 inches. In other embodiments, the length 806 may be outside of this range. The strap 800 is operably configured to at surround the user's limb and facilitate in the un-assisted coupling of the gel-pack 100 to a user's injured area of the user's limb. More specifically, with brief reference to FIGS. 1 and 9, the strap 800 is operably configured to surround the user-contact surface 204 and the user's injured limb so that said surface 204 is in contact with the limb to effectively and conveniently transfer pain-relieving hot or cold therapy. The strap 800 provides a significant advantage over prior-art devices, such as those which require a user to manually hold a gel-pack body, by permitting the user to have free range of motion with respect to the injured limb to perform select tasks. The strap 800 also advantageously decreases the risk of skin burns to the user's hands which may occur as a result of manually holding an ice pack or heating pad.

In order to effectively couple the first end 802 of the strap 800 to the second end 804 of the strap 800, in one embodiment, the strap 800 includes one or more fasteners. Although FIG. 8 depicts the fastener 808 as a hook-and-loop pad, the fastener 808 may be, without limitation, an adhesive, a snap fastener, an insert, a button, or another suitable fastening mechanism. In the same vein, the strap 800 may be made of nylon, neoprene, cotton, or another material which may or may not include additional padding to provide comfort and prevent chaffing of the user's skin when worn by the user.

Figure 10:
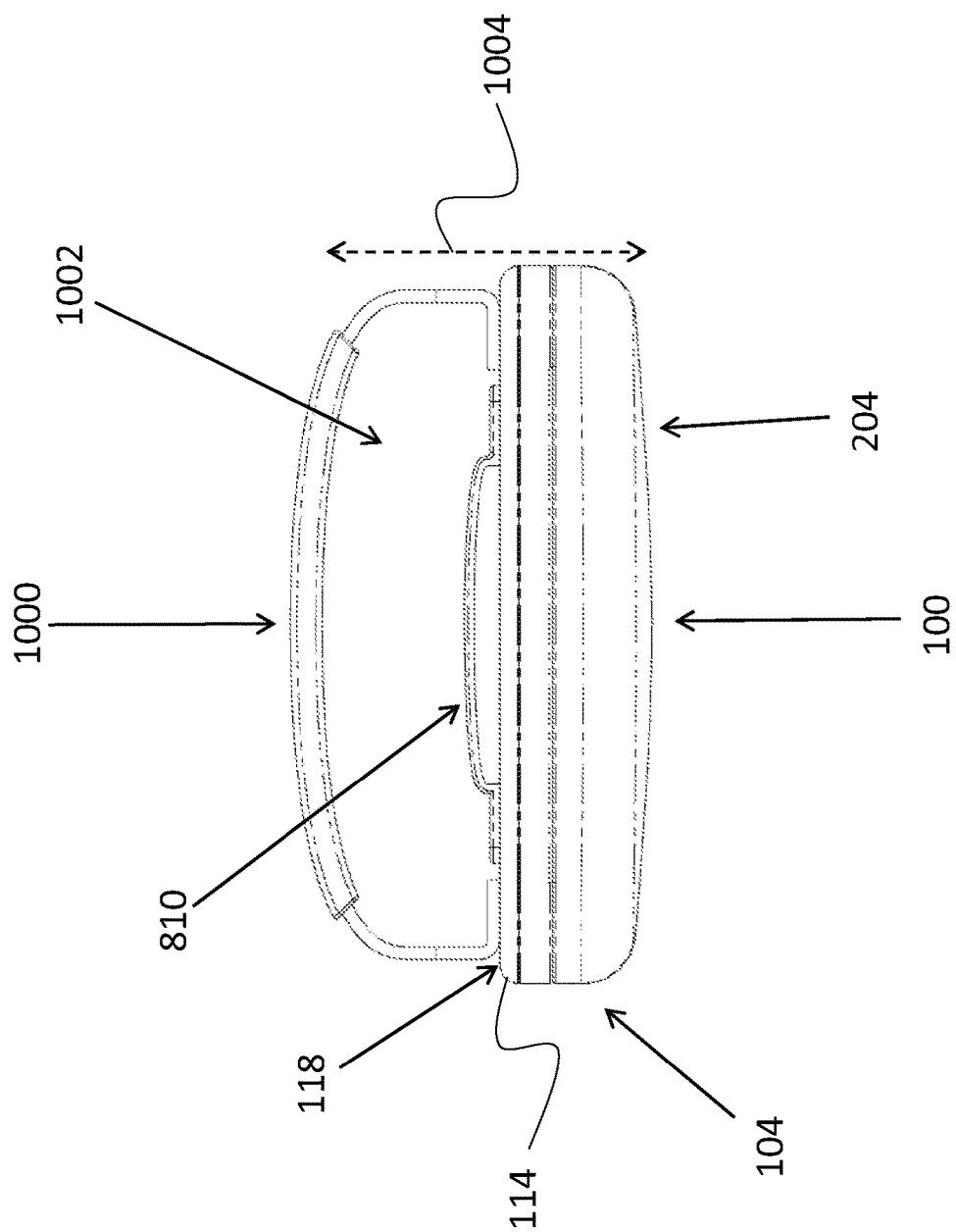
FIG. 10 is a top plan view of the gel-pack of FIG. 1 depicting a loop sized to receive the strap therein and a handle coupled to the second member in accordance with the present invention.

In one embodiment, the strap 800 is couplable to the outer surface 118 of the second member 114 at a location along the strap length 806. More specifically, the second member 114 may include a loop 810 coupled to the outer surface 118 of the second member 114. With reference to FIGS. 8 and 10, the loop 810 is sized to receive the strap 800 therein along the strap length 806 such that the first and second ends 802, 804 are free to couple to each other around the user's limb. Naturally, the location along the strap length 806 may vary according to the overall strap length 806, the size of the user's limb, and the like. In one embodiment, the strap 800 may be removably couplable to the outer surface 118 of the second member 114. For example, the first or second ends 802, 804 of the strap 800 may be pulled through a loop 810 formed on the back surface 118 of the body 102. In another embodiment, the strap 800 may be fixedly coupled to the second member 114 or another portion of the body 102. In one embodiment, the loop 810 is made of a cotton material. In another embodiment, the loop 810 may be made of neoprene, microfiber or another suitable material that may be the same or different from the material of the second member 114.

Figure 11:
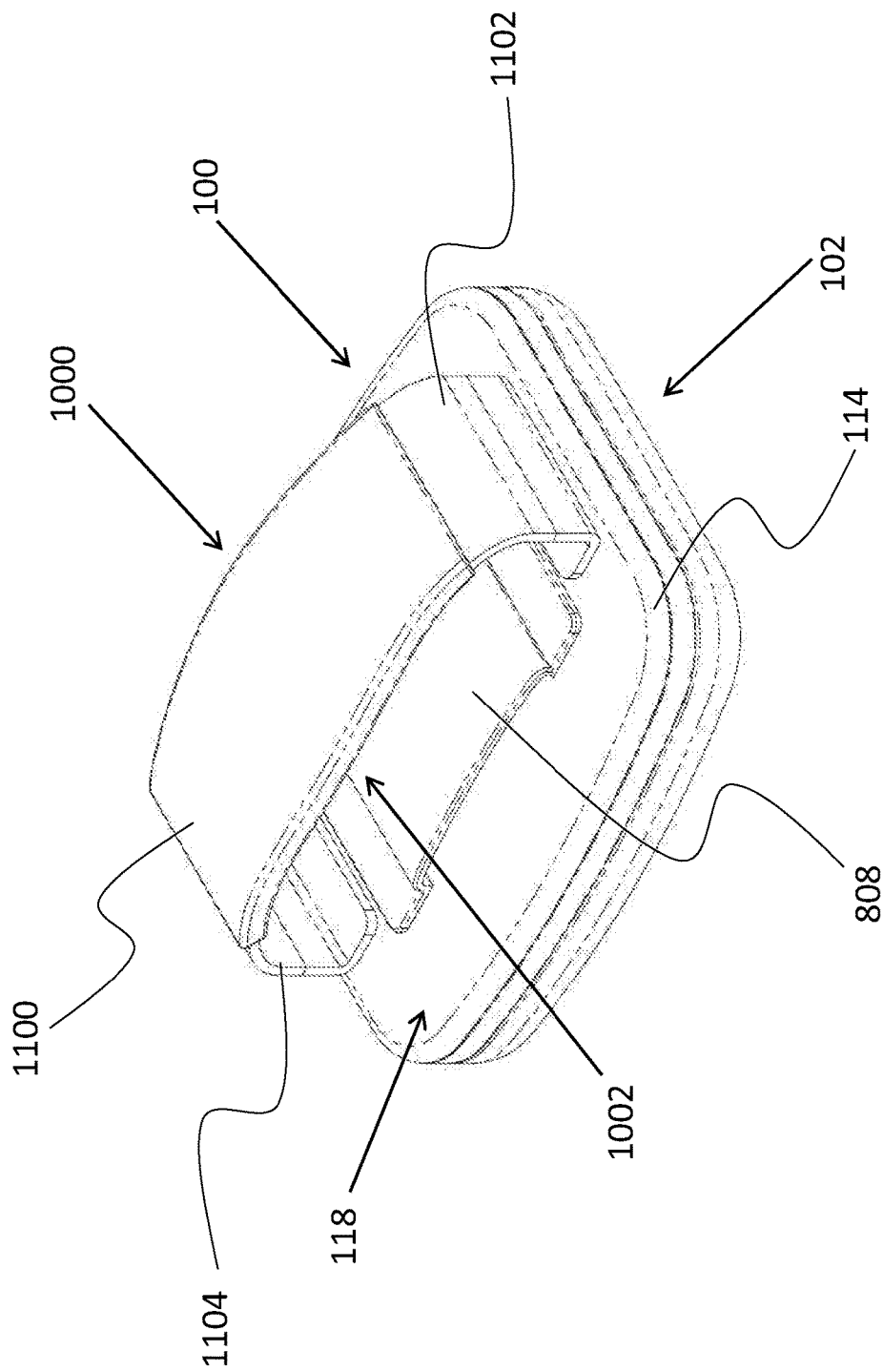
FIG. 11 is a perspective rear view of the gel-pack of FIG. 1 depicting the handle having at least one elastic member defining an adjustable circumference of the handle in accordance with the present invention.
Figure 12:
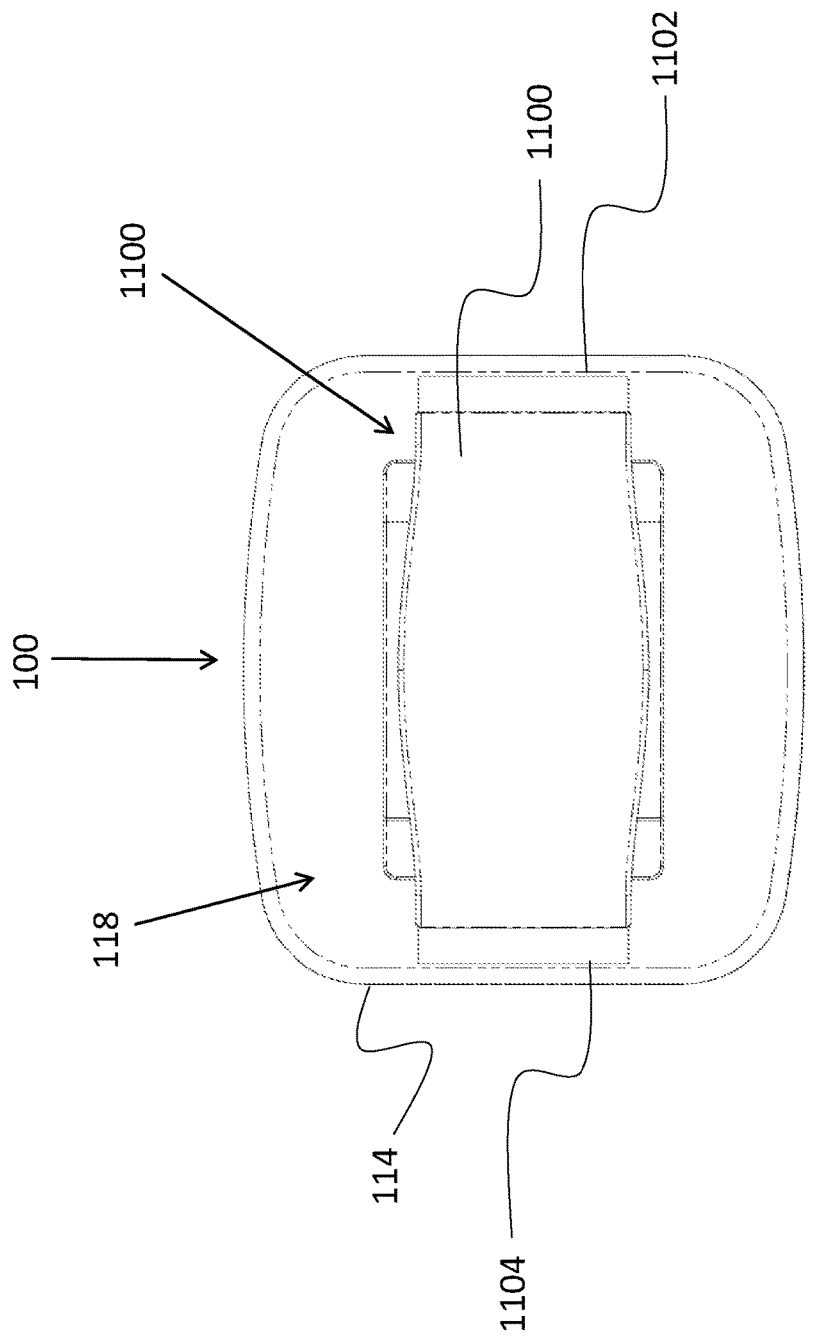
FIG. 12 is an elevational rear view of the gel-pack of FIG. 1 depicting the handle having a pair of elastic members in accordance with the present invention.

With reference now to FIGS. 10-12, the thermal gel-pack 100 can be seen having a handle 1000 coupled to the outer surface 118 of the second member 114. In one embodiment, the handle 1000 may be coupled to the outer surface 118 using an adhesive. In other embodiments, the handle 1000 may be coupled to the outer surface 118 using a hook-and-loop fastener, bolt, nail, or another suitable fastening mechanism that preferably does not penetrate through the second member 114 so as to avoid creating an aperture in the second member 114 that would cause water to leak from the container 110 (FIG. 1). The handle 1000 may be coupled to other portions of the thermal gel-pack 100 and is not limited to being coupled to the outer surface 118 of the second member 114. In one embodiment, the thermal gel-pack 100 includes an overall width 1004 spanning from the front surface 204 of the first portion 104 to the handle 1000. In one embodiment, the width 1004 is approximately 2-3 inches. In other embodiments, the width 1004 may be outside of this range.

In one embodiment, the handle 1000 defines a handle aperture 1002 configured to receive a portion of a user's hand, e.g., the fingers, entire hand, or the like, therein. The handle aperture 1002 provides the user with the ability to manually hold the gel-pack body 102 which may be advantageous when, for example, the user's injury is at a location that is not conducive for receiving the strap 800 (FIG. 8). When the user desires to utilize the strap 800 (FIG. 8), the handle aperture 1002 provides the user with a gripping surface for holding the gel-pack body 102 to conveniently insert the strap 800 through the loop 810.

In order to accommodate various hand sizes and shapes, the handle 1000 may include an adjustable handle strap 1100 defining an adjustable circumference of the handle aperture 1002. At least one elastic member 1102 can be seen integral with the handle strap 1100 to adjust the overall area of the handle aperture 1002. In a preferred embodiment, the handle strap 1100 includes a pair of elastic members 1102, 1104 disposed on opposing sides of the handle strap 1100. In another embodiment, one or more of the elastic members 1102, 1104 may be removably coupled to the handle strap 1100 or the handle strap 1100 may be non-adjustable. Said another way, the handle strap 1100 may define a non-adjustable circumference of the handle aperture 1002 and be devoid of the elastic members 1102, 1104.

A thermal gel-pack has been disclosed that includes a first portion having a gel cavity encapsulating a gel material and a second portion fluidly uncoupled from the first portion and including a container for storing a cold constituent, such as ice, therein. The gel material may be heated, or preferably frozen, to effectively supply hot or cold pain-relief therapy to treat an injury. In addition, embodiments of the invention provide a strap for encapsulating a user's injured limb so as to provide a user with the ability to use the thermal gel-pack strap hands-free.

What is claimed is:
1. A wearable thermal gel-pack comprising:
a gel-pack body having:
  a first portion including an inner surface and defining a gel cavity, the first portion encapsulating a gel material within the gel cavity; and
  a second portion with a container with a first member coupled to the first portion of the gel-pack body and having a proximal end, a distal end opposing the proximal end of the first member of the second portion, having opposing sides, and a continuous outer perimeter edge surrounding the opposing sides of the second portion and the distal end of the first member, a second member having a lower end pivotally coupled at the proximal end of the first member to form a joint, having a distal end opposing the lower end of the second member, having opposing sides, a continuous outer perimeter edge surrounding the opposing sides and the distal end of the second member, and with an outer surface opposing the inner surface of the first portion of the gel-pack body, and a container cavity defined by the first and second members of the container, the container cavity juxtaposed to and fluidly uncoupled to the gel cavity, the first and second members of the container having a closed position with the continuous outer perimeter edges thereon in a watertight configuration with respect to one another and operably configured to pivotally translate about the joint to have an open position:
    with a container opening continuously defined by and spanning the continuous outer perimeter edges on the first and second members of the second portion and with the continuous outer perimeter edges on the first and second members of the second portion separated from one another around the opposing sides and the distal ends of the first and second members of the second portion until reaching the joint;
with a portion of the container opening disposed proximal to the distal ends of the first and second members of the second portion in fluid communication with the container cavity; and
with the first and second members each with a side coupling material having opposing ends coupled to the first and second members of the second portion, respectively; and
a strap couplable to the outer surface of the second member at a location along a strap length and operably configured to surround a portion of a user's limb.

2. The wearable thermal gel-pack according to claim 1, wherein:
the first portion includes a front surface opposing the inner surface of the first portion such that the inner surface is interposed between the front surface of the first portion and the outer surface of the second member of the second portion, the front surface of an elastically deformable material.

3. The wearable thermal gel-pack according to claim 2, wherein:
the gel cavity is interposed between the front surface and the inner surface of the first portion.

4. The wearable thermal gel-pack according to claim 1, wherein:
the container cavity is interposed between the inner surface of the first portion and the outer surface of the second member of the second portion.

5. The wearable thermal gel-pack according to claim 1, wherein:
the gel material is one of hydroxyethyl cellulose, silica gel, and polymer.

6. The wearable thermal gel-pack according to claim 1, wherein:
the strap is removably couplable to the outer surface of the second member.

7. The wearable thermal gel-pack according to claim 1, further comprising:
a loop coupled to the outer surface of the second member, the loop sized to receive the strap therein along the strap length.

8. The wearable thermal gel-pack according to claim 1, further comprising:
a handle coupled to the outer surface of the second member, the handle defining a handle aperture configured to receive a portion of a user's hand therein.

9. The wearable thermal gel-pack according to claim 8, wherein:
the handle includes an adjustable handle strap defining an adjustable circumference of the handle aperture.

10. A wearable thermal gel-pack comprising:
a gel-pack body including:
a first portion having a user contact surface and an inner surface opposite the user contact surface, the user contact surface and the inner surface defining a gel cavity for encapsulating a gel material within the gel cavity;
a second portion having a container, the container including a first member coupled to the first portion of the gel-pack body and having a proximal end, a distal end opposing the proximal end of the first member of the second portion, having opposing sides, and a continuous outer perimeter edge surrounding the opposing sides of the second portion and the distal end of the first member, and a second member having a lower end pivotally coupled at the proximal end of the first member to form a joint, the second member having an outer surface opposing the inner surface of the first portion of the gel-pack body, having a distal end opposing the lower end of the second member, and having opposing sides, a continuous outer perimeter edge surrounding the opposing sides and the distal end of the second member;
a container cavity defined by the first and second members of the container, the container cavity substantially adjacent to and fluidly uncoupled to the gel cavity, the first and second members of the container having a closed position with the continuous outer perimeter edges thereon in a watertight configuration with respect to one another and operably configured to pivotally translate about the joint to have an open position:
with a container opening continuously defined by and spanning the continuous outer perimeter edges on the first and second members of the second portion and with the continuous outer perimeter edges on the first and second members of the second portion separated from one another around the opposing sides and the distal ends of the first and second members of the second portion until reaching the joint;
with a portion of the container opening disposed proximal to the distal ends of the first and second members of the second portion in fluid communication with the container cavity; and
with the first and second members each with a side coupling material having opposing ends coupled to the first and second members of the second portion, respectively; and
a loop coupled to the outer surface of the second member, the loop sized to receive a strap therein along a strap length, the strap operably configured to couple the user contact surface of the first portion to a portion of a user's limb.

11. The wearable thermal gel-pack according to claim 10, wherein:
the user contact surface of the first portion is of an elastically deformable material.

12. The wearable thermal gel-pack according to claim 10, wherein:
the gel cavity is interposed between the user contact surface and the inner surface of the first portion.

13. The wearable thermal gel-pack according to claim 10, wherein:
the container cavity is interposed between the inner surface of the first portion and the outer surface of the second member of the second portion.

14. The wearable thermal gel-pack according to claim 10, wherein:
the gel material is one of hydroxyethyl cellulose, silica gel, and polymer.

15. The wearable thermal gel-pack according to claim 10, wherein:
the strap includes a first end and a second end opposite the first end along the strap length.

16. The wearable thermal gel-pack according to claim 10, further comprising:
a handle coupled to the outer surface of the second member, the handle defining a handle aperture configured to receive a portion of a user's hand therein.

17. The wearable thermal gel-pack according to claim 16, wherein:

the handle includes an adjustable handle strap defining an adjustable circumference of the handle aperture.

\* \* \* \* \*